(12) United States Patent
Wang

(10) Patent No.: US 11,931,488 B1
(45) Date of Patent: Mar. 19, 2024

(54) NEBULIZING DIFFUSER

(71) Applicant: ShenZhen ChangLin Houseware Co., Ltd., Shenzhen (CN)

(72) Inventor: Wen Wang, Shenzhen (CN)

(73) Assignee: ShenZhen ChangLin Houseware Co., Ltd., Shenzhen (CN)

(*) Notice: Subject to any disclaimer, the term of this patent is extended or adjusted under 35 U.S.C. 154(b) by 0 days.

(21) Appl. No.: 18/447,994

(22) Filed: Aug. 10, 2023

(30) Foreign Application Priority Data

Jul. 26, 2023 (CN) .......................... 202321992236.9

(51) Int. Cl.
*A61L 9/14* (2006.01)

(52) U.S. Cl.
CPC ........... *A61L 9/14* (2013.01); *A61L 2209/133* (2013.01); *A61L 2209/134* (2013.01)

(58) Field of Classification Search
CPC . A61L 9/14; A61L 2209/133; A61L 2209/134
See application file for complete search history.

(56) References Cited

U.S. PATENT DOCUMENTS

| | | | |
|---|---|---|---|
| 2010/0308129 A1* | 12/2010 | Jorgensen | B05B 7/0012 239/34 |
| 2012/0251296 A1* | 10/2012 | Jorgensen | B05B 17/0607 415/116 |
| 2014/0049941 A1* | 2/2014 | Lee | A61L 9/122 362/96 |
| 2018/0103507 A1* | 4/2018 | Davis | H05B 3/0004 |

FOREIGN PATENT DOCUMENTS

| | | |
|---|---|---|
| CN | 210673859 U | 6/2020 |
| CN | 216897639 U | 7/2022 |
| CN | 216897706 U | 7/2022 |

* cited by examiner

*Primary Examiner* — Sean E Conley
*Assistant Examiner* — Brendan A Hensel

(57) ABSTRACT

Disclosed is a nebulizing diffuser, including a shell, an air pump, a bottle seat, and an atomizing cavity, where a bottom of the bottle seat is provided with a first oil outlet and a first oil return hole; a top of the atomizing cavity is provided with a second oil outlet and a second oil return hole; the first oil outlet and the second oil outlet are connected with each other up and down; the first oil return hole and the second oil return hole are connected with each other up and down; a lateral portion of the atomizing cavity is provided with an air wave hole; and the shell is provided with a mist outlet. The nebulizing diffuser can discharge essential oil mist efficiently, and can make full use of essential oil in the bottle.

8 Claims, 9 Drawing Sheets

NEBULIZING DIFFUSER

CROSS-REFERENCE TO RELATED APPLICATIONS

The application claims priority to Chinese patent application No. 2023219922369, filed on Jul. 26, 2023, the entire contents of which are incorporated herein by reference.

TECHNICAL FIELD

The present application relates to an essential oil diffusion device, and particularly relates to a nebulizing diffuser.

BACKGROUND

An essential oil diffusion device is a device through which essential oil is volatilized, such that a fragrance is generated in a surrounding air environment. Related structures refer to a public document of a Chinese patent tiled "Conveniently disassembled and assembled essential oil diffuser" with the publication number CN210673859U. It has recorded:

"the aroma diffusing head 6 is provided with an aroma guiding column 13, the aroma guiding column 13 is provided with an aroma guiding hole 14, the thread mounting portion 10 is provided with an aroma guiding assembly 15, the aroma guiding hole 14 is connected with the aroma guiding assembly 15, and the aroma guiding assembly 15 is embedded into an opening of the essential oil bottle 7; the aroma guiding assembly 15 includes an aroma guiding pad 16, a fixed head 17 and an aroma guiding cotton sliver 18, where the aroma guiding pad 16 and the fixed head 17 are respectively mounted in the thread mounting portion 10, and one end of the aroma guiding cotton sliver is fixed in the fixed head 17 and the other end thereof is inserted into the essential oil bottle 7."

In this kind of structure, essential oil in the essential oil bottle needs to be sucked out through a tube. The essential oil flows from bottom to top. In an actual application, the essential oil in the essential oil bottle can be thoroughly sucked only when the essential oil bottle and the tube are long enough to touch the bottle of the bottle. If the length of the tube is designed improperly, the essential oil will be wasted. In addition, most existing essential oil diffusion devices make the essential oil be volatilized naturally, so that the essential oil diffusion efficiency is extremely low, which cannot satisfy the application requirements.

SUMMARY

To overcome shortcomings in the prior art, the present application is to provide a nebulizing diffuser capable of efficiently discharging essential oil mist and making full use of essential oil in a bottle.

To solve the above technical problems, the present application adopts the following technical solution:

A nebulizing diffuser, including a shell, where the shell is internally provided with an air pump, a bottle seat and an atomizing cavity; the bottle seat is located at a top of the shell and is used for mounting an essential oil bottle; a bottom of the bottle seat is provided with a first oil outlet and a first oil return hole; a top of the atomizing cavity is provided with a second oil outlet and a second oil return hole, and the atomizing cavity is internally provided with an oil return tube connected with the second oil return hole; the oil return tube extends towards a direction of a bottom of the atomizing cavity; the atomizing cavity is fixed at the bottom of the bottle seat; the first oil outlet and the second oil outlet are connected with each other up and down, and the first oil return hole and the second oil return hole are connected with each other up and down; a lateral portion of the atomizing cavity is provided with an air wave hole connected with the air pump, the air pump conveys a high pressure air flow to the air wave hole, and the air wave hole is formed adjacent to the second oil outlet; the shell is provided with a mist outlet; and essential oil mist generated in the atomizing cavity is discharged through the mist outlet.

Preferably, a retainer ring is formed at the bottom of the bottle seat, the first oil outlet is located at an inner side of the retainer ring, and the first oil return hole is located at an outer side of the retainer ring.

Preferably, the bottom of the bottle seat is provided with a plurality of first oil outlets, and wide-mouth portions are formed at lower openings of the first oil outlets.

Preferably, an inserting tube head is formed at a lower end of the bottle seat, the first oil return hole is formed in an inner side of the inserting tube head, and the inserting tube head is in inserting fit with an upper end of the second oil return hole.

Preferably, an air tube connector is formed at the lateral portion of the atomizing cavity, the air wave hole is formed at an inner side of the air tube connector, and the air tube connector is connected to the air pump through an air tube.

Preferably, the shell is internally provided with a buffer cavity, the buffer cavity is connected to the atomizing cavity, and the mist outlet is connected to the buffer cavity.

Preferably, two mist guide tubes are arranged at a bottom of the buffer cavity, and the two mist guide tubes both are connected to the atomizing cavity.

Preferably, the shell is internally provided with a printed circuit board (PCB) and a battery, and the air pump and the battery are electrically connected to the PCB, respectively.

Preferably, a screw mouth screwed with the essential oil bottle is formed at a top end of the bottle seat, a rubber plug is inserted at the bottom of the shell, and the rubber plug can be in inserting fit with the screw mouth.

Preferably, the bottom of the atomizing cavity is provided with a bottom cover, and the atomizing cavity and the bottom cover are fixedly connected through a screw.

According to the nebulizing diffuser disclosed by the present application, the essential oil bottle is a product purchased by a user and can be matched with the screw mouth on the bottle seat, and moreover, the essential oil bottle is mounted reversely, so that the essential oil can be fully fed into the first oil outlet. When the essential oil drops out downwards from the first oil return hole, a high pressure air flow in the air wave hole is blown to the essential oil dropping out from the second oil outlet from the lateral portion. Under the action of the high pressure air flow, essential oil atomization is accelerated, so that essential oil mist is formed in the atomizing cavity. Finally, the essential oil mist generated in the atomizing cavity is discharged from the mist outlet. Compared with the way of natural volatilization in the prior art, the present application improves the discharging efficiency of the essential oil mist greatly.

DETAILED DESCRIPTION OF THE EMBODIMENTS

Figure 1:
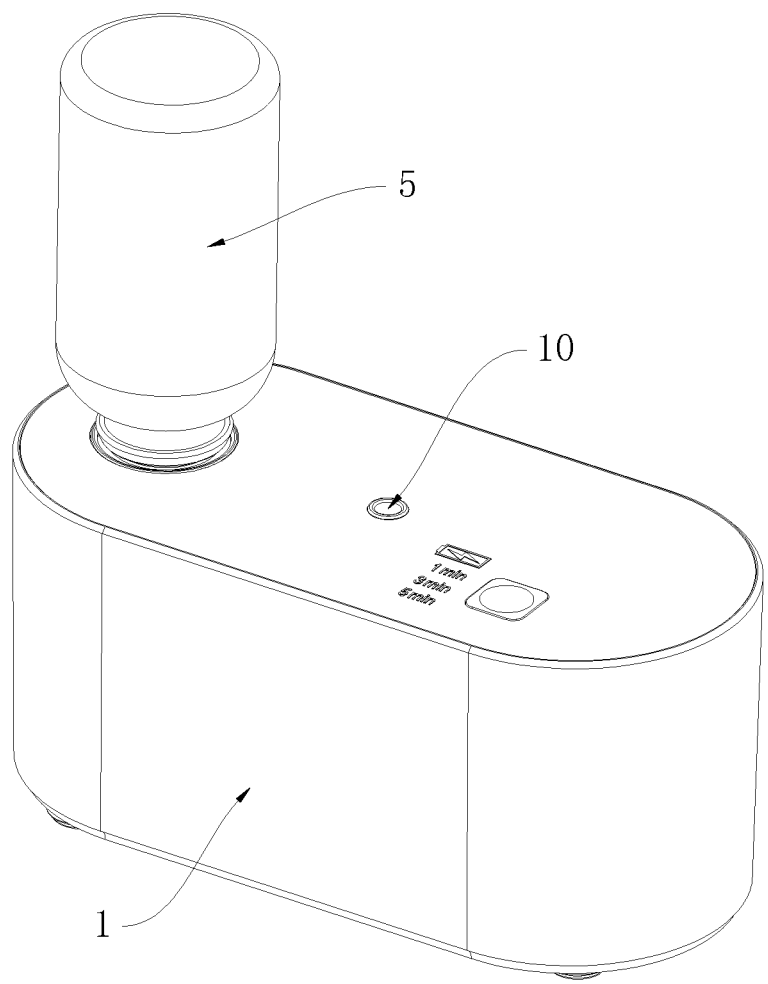
FIG. 1 is a three dimensional diagram of a nebulizing diffuser.

The present application will be further described in detail below in combination with drawings and embodiments.

The present application discloses a nebulizing diffuser, as shown in FIGS. 1-9, including a shell 1, where the shell 1 is internally provided with an air pump 2, a bottle seat 3 and an atomizing cavity 4; the bottle seat 3 is located at a top of the shell 1 and is used for mounting an essential oil bottle 5; a bottom of the bottle seat 3 is provided with a first oil outlet 30 and a first oil return hole 31; a top of the atomizing cavity 4 is provided with a second oil outlet 40 and a second oil return hole 41, and the atomizing cavity 4 is internally provided with an oil return tube 42 connected with the second oil return hole 41; the oil return tube 42 extends towards a direction of a bottom of the atomizing cavity 4; the atomizing cavity 4 is fixed at the bottom of the bottle seat 3; the first oil outlet 30 and the second oil outlet 40 are connected with each other up and down, and the first oil return hole 31 and the second oil return hole 41 are connected with each other up and down; a lateral portion of the atomizing cavity 4 is provided with an air wave hole 43 connected with the air pump 2, the air pump 2 conveys a high pressure air flow to the air wave hole 43, and the air wave hole 43 is formed adjacent to the second oil outlet 40; the shell 1 is provided with a mist outlet 10; and essential oil mist generated in the atomizing cavity 4 is discharged through the mist outlet 10.

In the above structure, the essential oil bottle 5 is a product purchased by a user and can be matched with a screw mouth 35 on the bottle seat 3, and moreover, the essential oil bottle 5 is mounted reversely, so that the essential oil can be fully fed into the first oil outlet 30. When the essential oil drops out downwards from the first oil return hole 31, a high pressure air flow in the air wave hole 43 is blown to the essential oil dropping out from the second oil outlet 40 from the lateral portion. Under the action of the high pressure air flow, essential oil atomization is accelerated, so that essential oil mist is formed in the atomizing cavity 4. Finally, the essential oil mist generated in the atomizing cavity 4 is discharged from the mist outlet 10. Compared with the way of natural volatilization in the prior art, the present application improves the discharging efficiency of the essential oil mist greatly. Meanwhile, the essential oil dropping into the atomizing cavity 4 will focus on the bottom of the atomizing cavity 4. With the essential oil within the essential oil bottle 5 dropping out gradually, under the siphon action, the essential oil close to the bottom of the atomizing cavity 4 is reversely sucked into the essential oil bottle 5 through the oil return tube 42, so that the essential oil comes in and goes out circularly. In an actual application, under the action of the high pressure air flow, a certain kinetic energy is also provided to the essential oil dropping out, so that the essential oil drops out consecutively from the second oil outlet 40.

Figure 7:
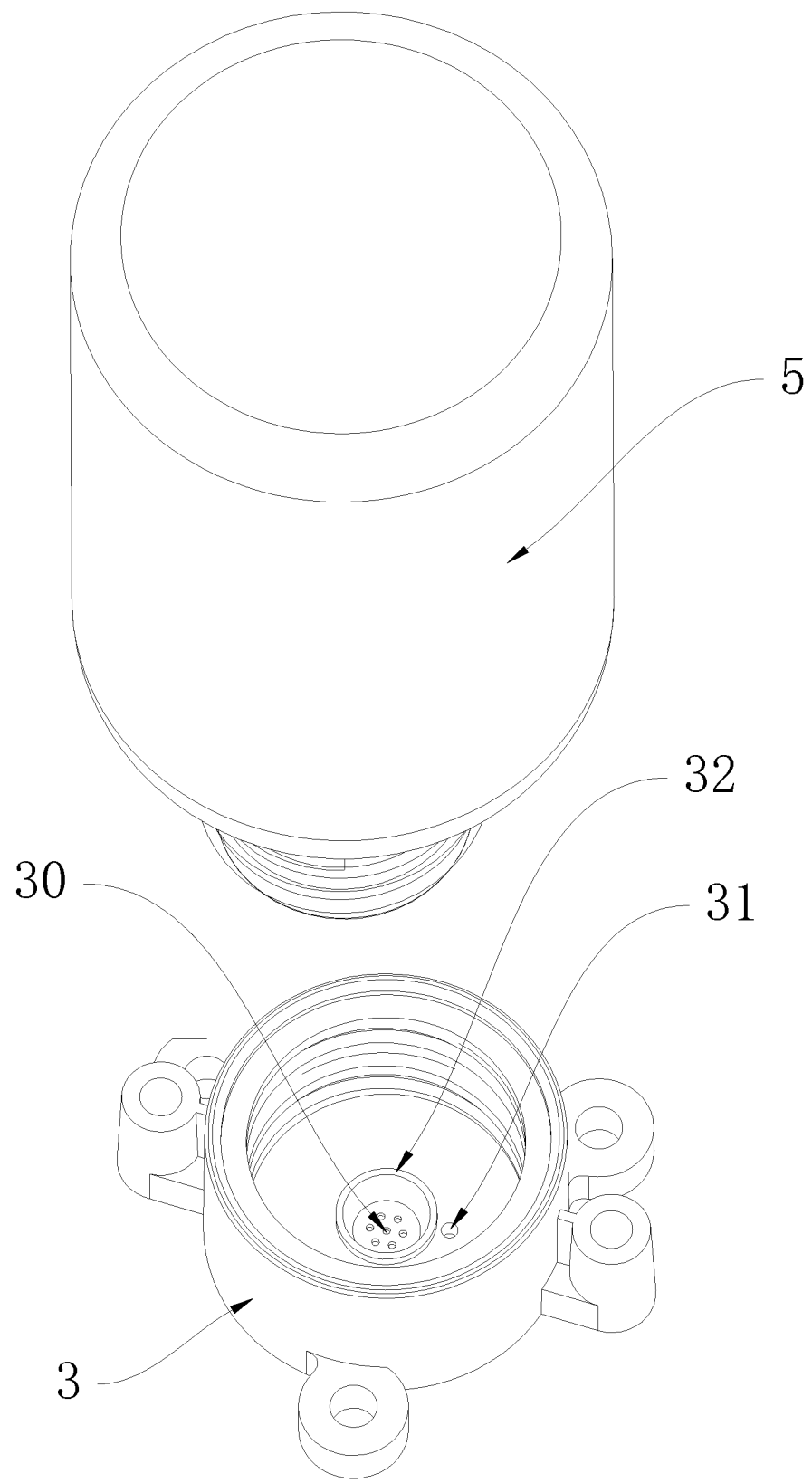
FIG. 7 is a structural diagram III of the bottle seat and the essential oil bottle.

Referring to FIG. 7, to better feed the essential oil, in the embodiment, a retainer ring 32 is formed at the bottom of the bottle seat 3, the first oil outlet 30 is located at an inner side of the retainer ring 32, and the first oil return hole 31 is located at an outer side of the retainer ring 32.

Further, the bottom of the bottle seat 3 is provided with a plurality of first oil outlets 30, and wide-mouth portions 33 are formed at lower openings of the first oil outlets 30. The open-mouth portions 33 are beneficial for the essential oil to be gathered towards the second oil outlet 40.

Figure 6:
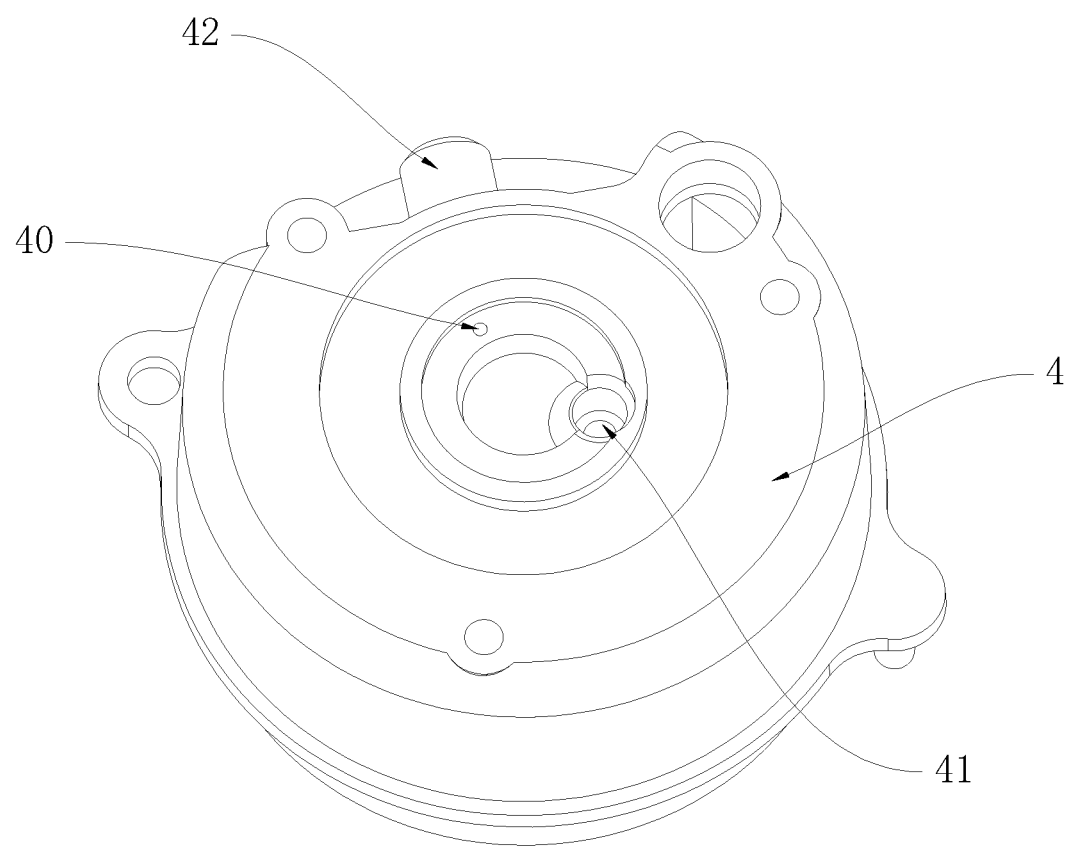
FIG. 6 is a three dimensional diagram II of the atomizing cavity.
Figure 8:
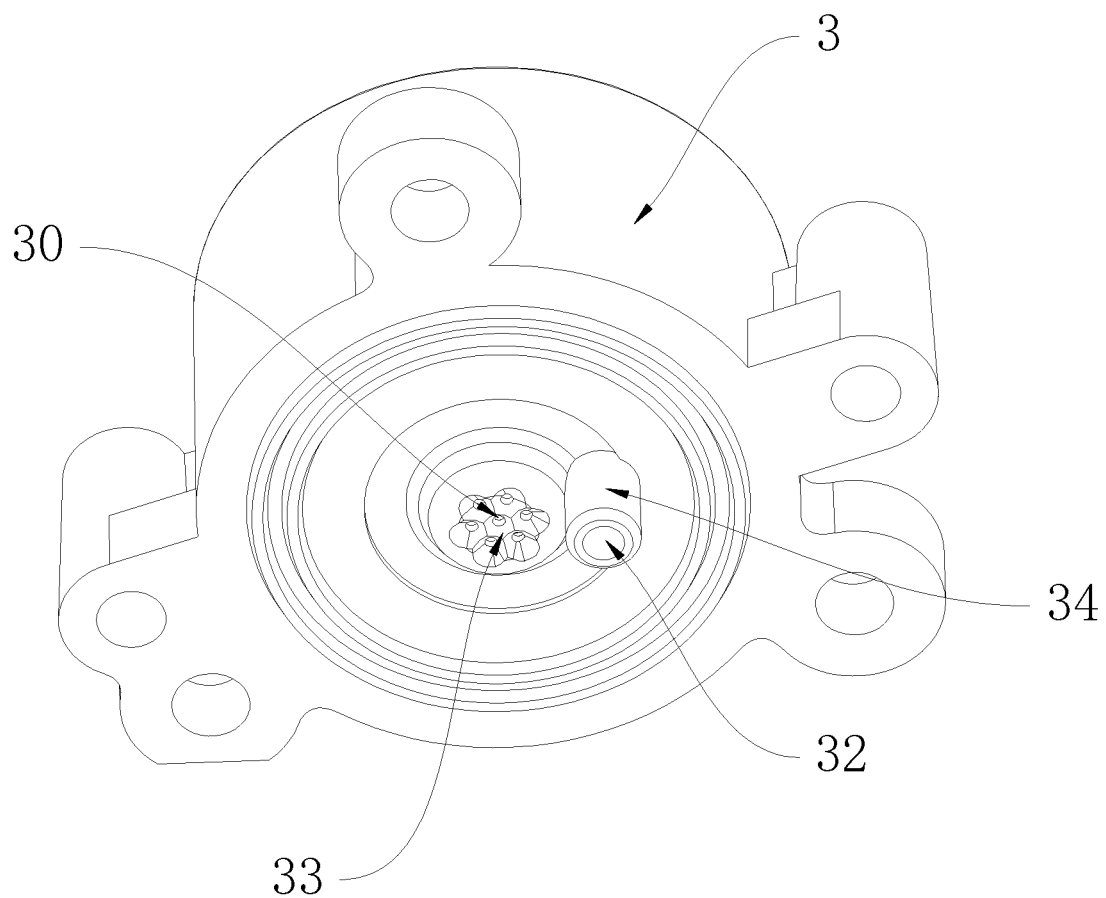
FIG. 8 is a three dimensional diagram of the bottle seat.

In combination with FIG. 6 and FIG. 8, to better separate an oil inlet circuit from an oil outlet circuit, in the embodiment, an inserting tube head 34 is formed at a lower end of the bottle seat 3, the first oil return hole 31 is formed in an inner side of the inserting tube head 34, and the inserting tube head 34 is in inserting fit with an upper end of the second oil return hole 41.

Figure 2:
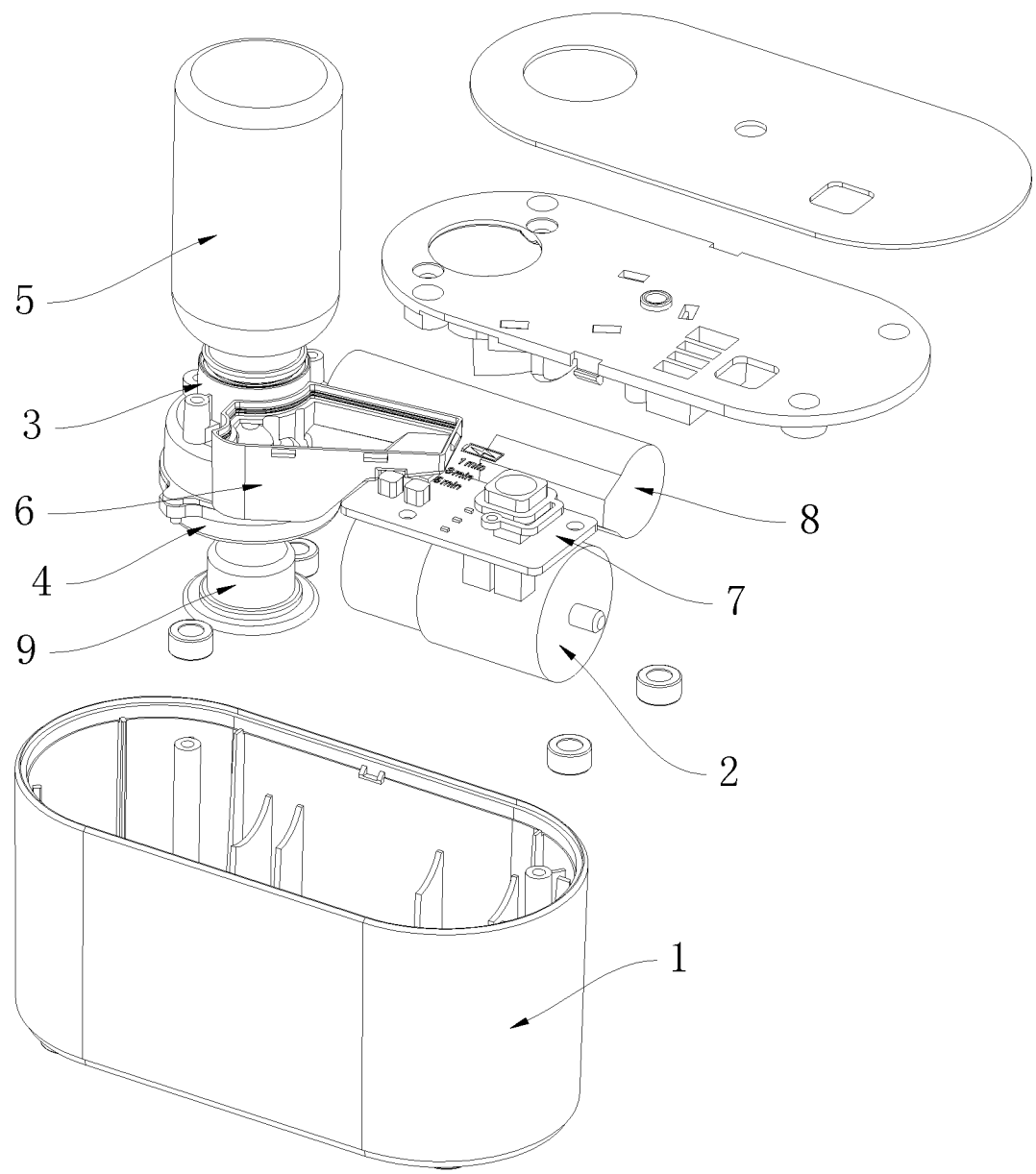
FIG. 2 is an exploded view of the nebulizing diffuser.
Figure 3:
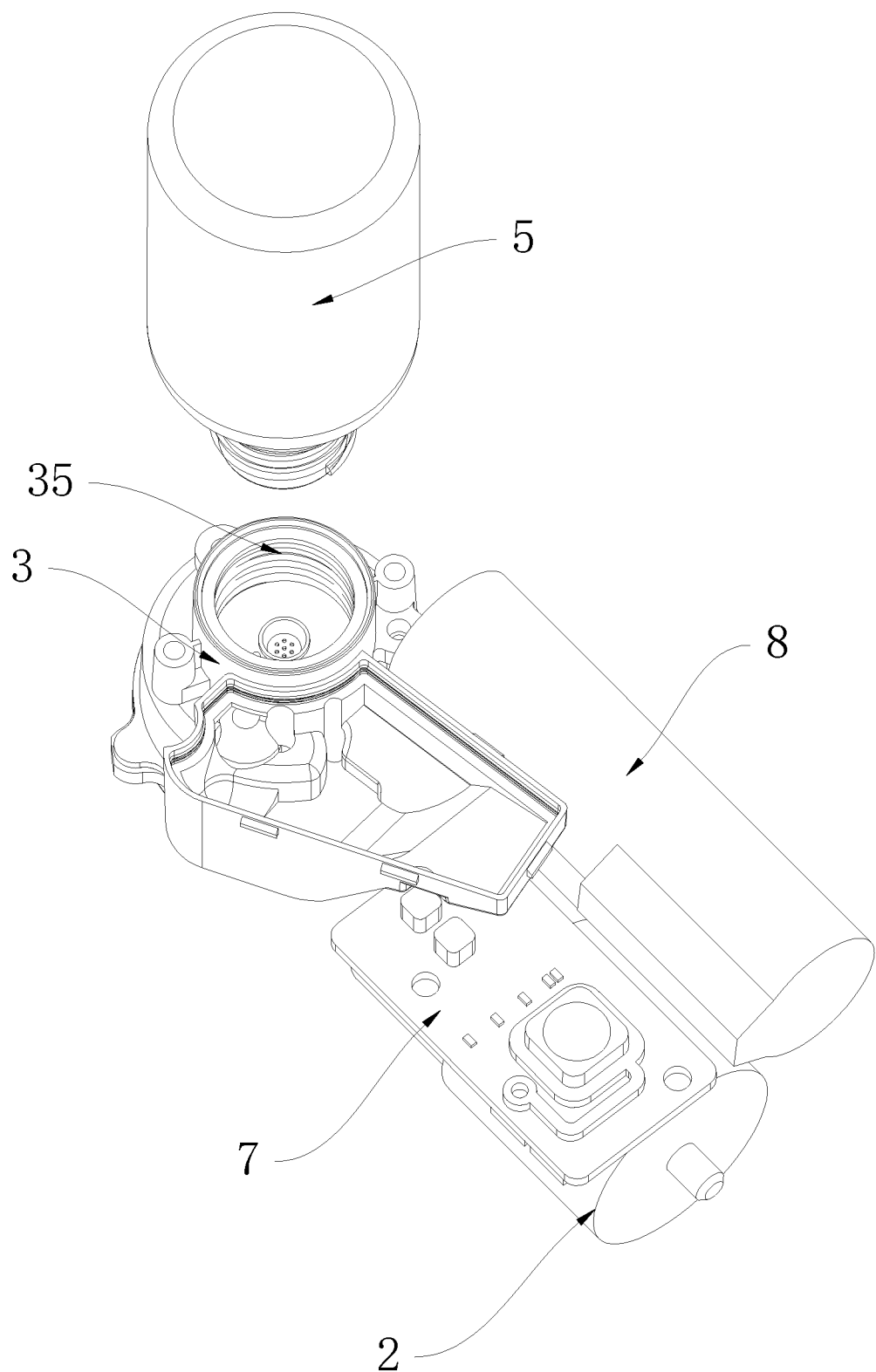
FIG. 3 is a structural diagram I of a bottle seat and an essential oil bottle.
Figure 4:
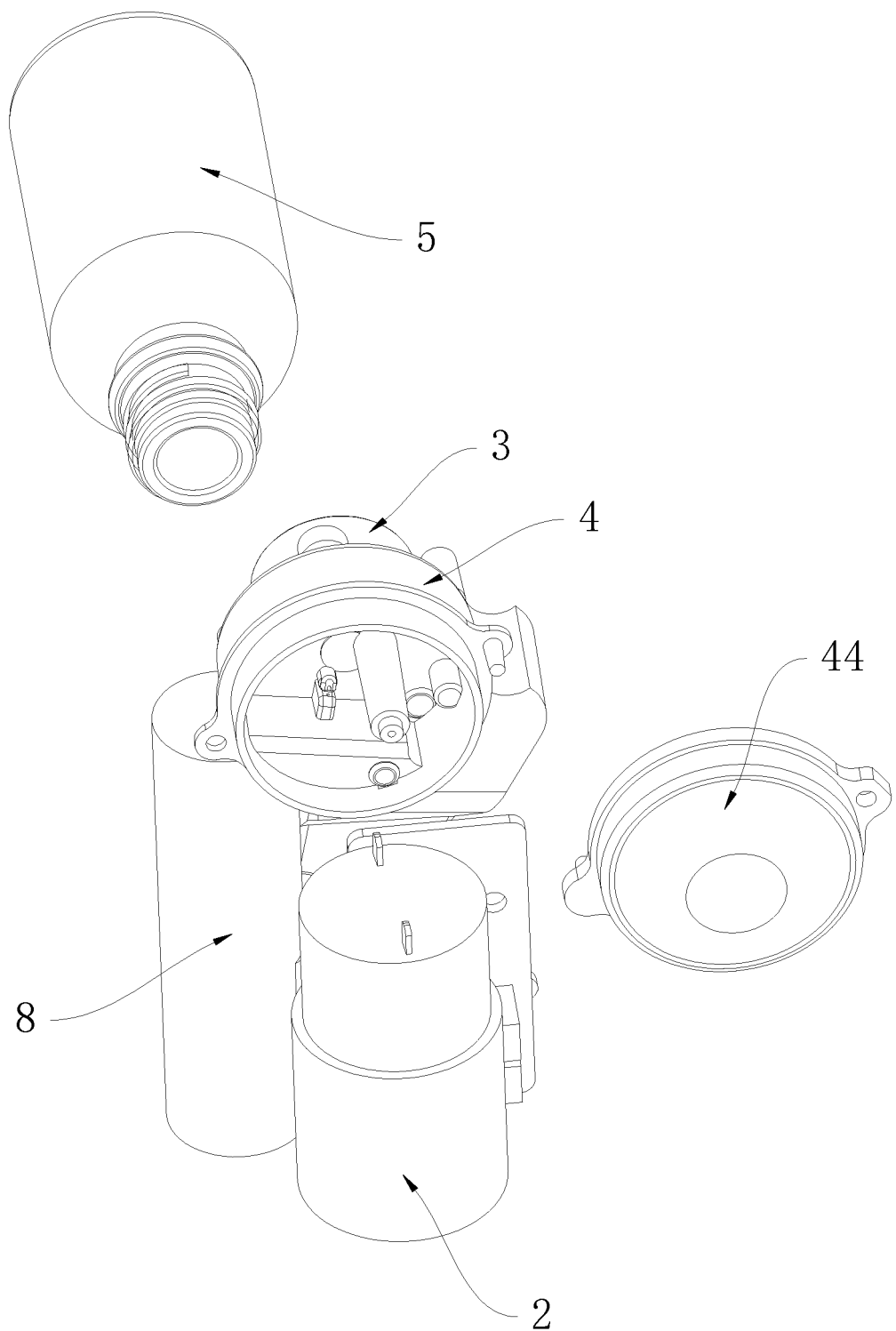
FIG. 4 is a structural diagram II of the bottle seat and the essential oil bottle.

In combination with FIG. 2 and FIG. 6, as a preferred mode, an air tube connector 42 is formed at the lateral portion of the atomizing cavity 4, the air wave hole 43 is formed at an inner side of the air tube connector 42, and the air tube connector 42 is connected to the air pump 2 through an air tube.

Figure 5:
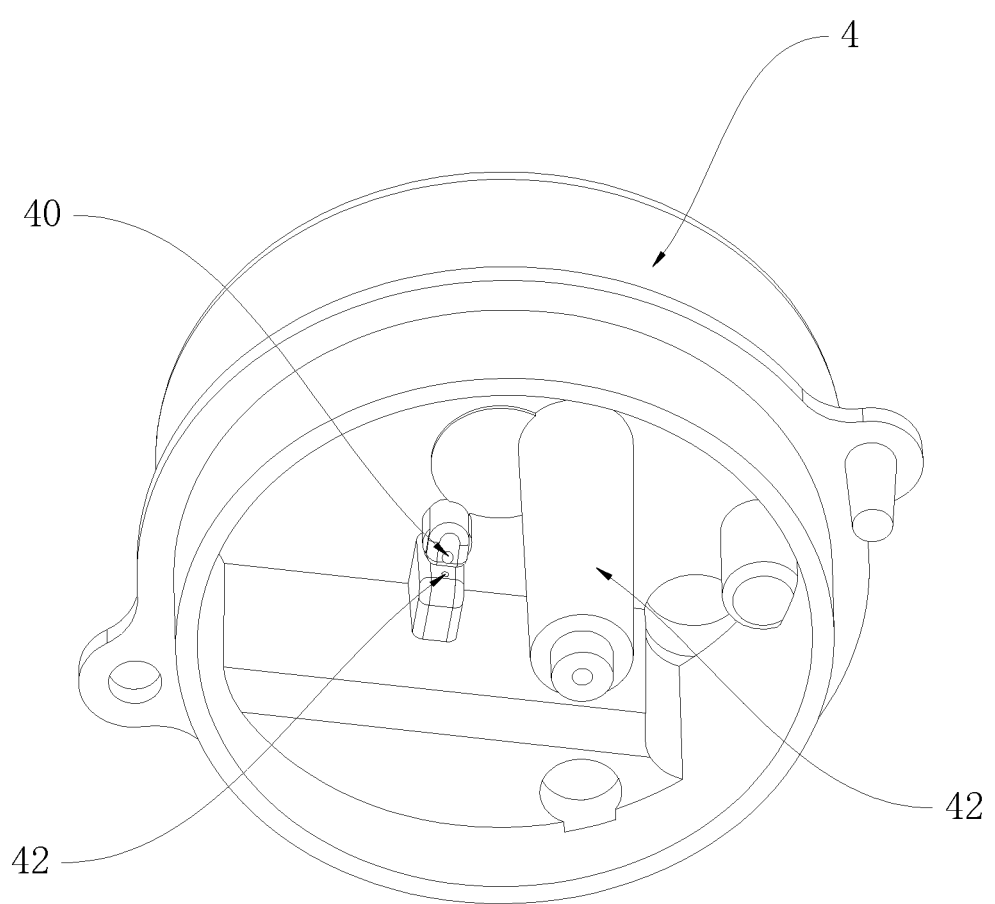
FIG. 5 is a three dimensional diagram I of an atomizing cavity.

Referring to FIG. 5, in the embodiment, the air wave hole 43 is adjacent to the second oil outlet 40. Specifically speaking, the air wave hole 43 blows out a lateral air flow. The second oil outlet 40 faces downwards vertically. The direction of the lateral air flow is perpendicular to the opening direction of the second oil outlet 40 or forms an acute angle or an obtuse angle therewith. As long as there is a certain angle between the lateral air flow and the opening direction of the second oil outlet 40, it can be guaranteed that the lateral air flow acts on the dropping essential oil and generates the essential oil mist.

Figure 9:
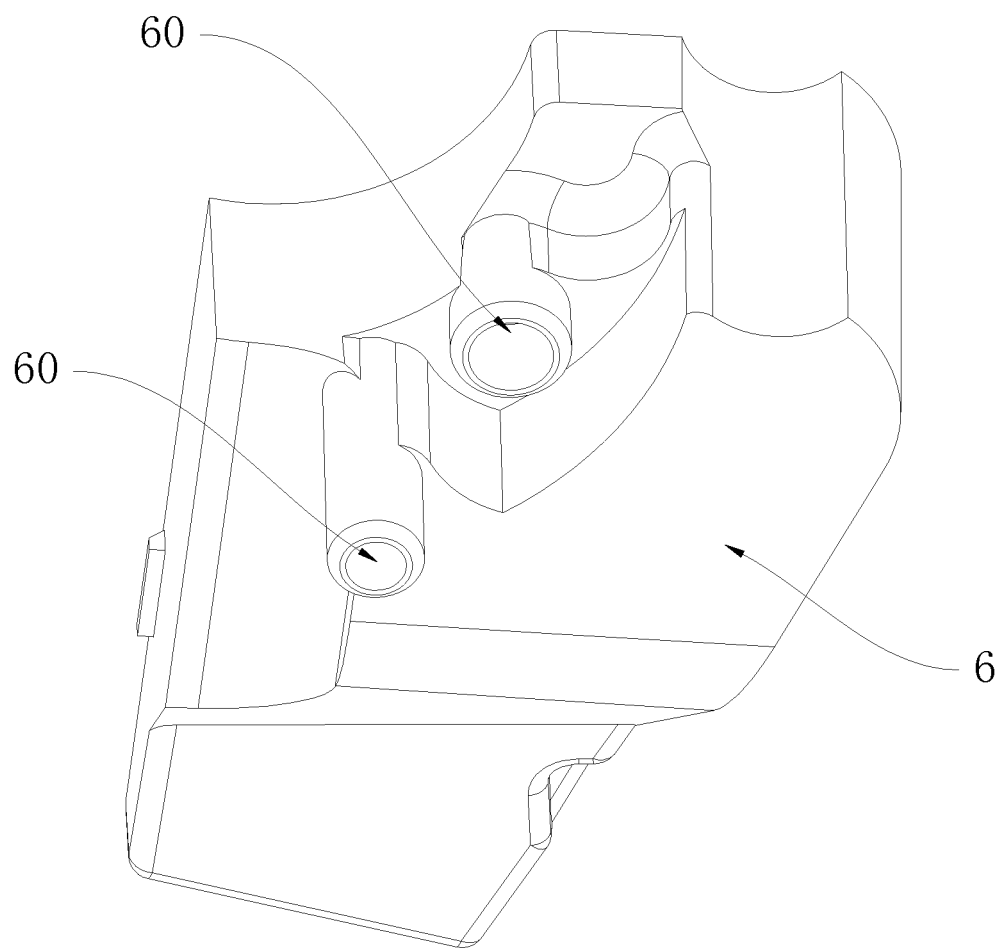
FIG. 9 is a three dimensional diagram of a buffer cavity.

In combination with FIG. 2 and FIG. 9, in the embodiment, the shell 1 is internally provided with a buffer cavity 6, the buffer cavity 6 is connected to the atomizing cavity 4, and the mist outlet 10 is connected to the buffer cavity 6. In the above structure, the buffer cavity 6 plays a role of collecting the essential oil mist discharged from the atomizing cavity 4. After the buffer cavity 6 is filled with the essential oil mist, the essential oil mist is then discharged from the mist outlet 10. In the embodiment, by arranging the buffer cavity 6, the essential oil mist can be temporarily stored and buffered, so that the essential oil discharged through the mist outlet 10 is further balanced.

To better connect the atomizing cavity 4, in the embodiment, two mist guide tubes 60 are arranged at a bottom of the buffer cavity 6, and the two mist guide tubes 60 both are connected to the atomizing cavity 4.

With respect to other structures in the shell 1, referring to FIG. 2, the shell 1 is internally provided with a printed circuit board (PCB) 7 and a battery 8, and the air pump 2 and the battery 8 are electrically connected to the PCB 7, respectively. Specifically, the top of the shell 1 is further provided with a button electrically connected to the PCB 7.

Referring to FIG. 2, as a preferred structure, a screw mouth 35 screwed with the essential oil bottle 5 is formed at a top end of the bottle seat 3, a rubber plug 9 is inserted at the bottom of the shell 1, and the rubber plug 9 can be in inserting fit with the screw mouth 35. Specifically speaking, the bottom of the shell 1 is provided with an insertion opening capable of accommodating the rubber plug 9. When the bottle seat 3 is screwed with the essential oil bottle 5, the rubber plug 9 is inserted into the insertion opening at the bottom of the shell 1. When the essential oil bottle 5 is taken down from the bottle seat 3, the screw mouth 35 of the bottle seat 3 is blocked with the rubber plug 9, thereby playing a protecting role.

To clean the inner side of the atomizing cavity 4 conveniently, in the embodiment, the bottom of the atomizing cavity 4 is provided with a bottom cover 44, and the atomizing cavity and the bottom cover are fixedly connected through a screw.

The nebulizing diffuser disclosed by the present application has no limitation on formula, type and fragrance of the essential oil in the essential oil bottle and can be matched with essential oil bottles widely sold on the market. Meanwhile, in the present application, it is unnecessary to heat the essential oil or to subject the essential oil to other treatments, so that the essential oil is diffused in the form of original ecology. In addition, the essential oil bottle in the present application is mounted reversely, which better avoids waste caused by residues of the essential oil. It can be seen from the above characteristics that the present application has a prominent progress in the field of essential oil diffusion devices, is suitably popularized and applied on the market, and has a better market prospect.

The above mentioned is merely the preferred embodiments of the present application and is not intended to limit the present application. Modifications, equivalent substitutions or improvements made within the technical scope of the present application shall be included in the scope of protection of the present application.

What is claimed is:

1. A nebulizing diffuser, comprising a shell, wherein the shell is internally provided with an air pump, a bottle seat and an atomizing cavity; the bottle seat is located at a top of the shell and is used for mounting an essential oil bottle; a bottom of the bottle seat is provided with a first oil outlet and a first oil return hole; a top of the atomizing cavity is provided with a second oil outlet and a second oil return hole, and the atomizing cavity is internally provided with an oil return tube connected with the second oil return hole; the oil return tube extends towards a direction of a bottom of the atomizing cavity; the atomizing cavity is fixed at the bottom of the bottle seat; the first oil outlet and the second oil outlet are connected with each other, and the first oil return hole and the second oil return hole are connected with each other; a lateral portion of the atomizing cavity is provided with an air wave hole connected with the air pump, the air pump conveys a air flow to the air wave hole, and the air wave hole is formed adjacent to the second oil outlet; the shell is provided with a mist outlet; and essential oil mist generated in the atomizing cavity is discharged through the mist outlet, wherein the bottom of the bottle seat is provided with a plurality of first oil outlets, and wide-mouth portions are formed at lower openings of the first oil outlets.

2. The nebulizing diffuser according to claim 1, wherein a retainer ring is formed at the bottom of the bottle seat, the first oil outlet is located at an inner side of the retainer ring, and the first oil return hole is located at an outer side of the retainer ring.

3. The nebulizing diffuser according to claim 1, wherein an inserting tube head is formed at a lower end of the bottle seat, the first oil return hole is formed in an inner side of the inserting tube head, and the inserting tube head is in inserting fit with an upper end of the second oil return hole.

4. The nebulizing diffuser according to claim 1, wherein an air tube connector is formed at the lateral portion of the atomizing cavity, the air wave hole is formed at an inner side of the air tube connector, and the air tube connector is connected to the air pump through an air tube.

5. The nebulizing diffuser according to claim 1, wherein the shell is internally provided with a buffer cavity, the buffer cavity is connected to the atomizing cavity, and the mist outlet is connected to the buffer cavity.

6. The nebulizing diffuser according to claim 5, wherein two mist guide tubes are arranged at a bottom of the buffer cavity, and the two mist guide tubes both are connected to the atomizing cavity.

7. The nebulizing diffuser according to claim 1, wherein the shell is internally provided with a printed circuit board (PCB) and a battery, and the air pump and the battery are electrically connected to the PCB, respectively.

8. The nebulizing diffuser according to claim 1, wherein the bottom of the atomizing cavity is provided with a bottom cover, and the atomizing cavity and the bottom cover are fixedly connected through a screw.

\* \* \* \* \*